United States Patent [19]

Sanderson et al.

[11] Patent Number: 4,803,305

[45] Date of Patent: Feb. 7, 1989

[54] ISOBUTANE OXIDATION IN THE PRESENCE OF A SOLUBLE IRON COMPLEX AS CATALYST

[75] Inventors: John R. Sanderson, Leander; Edward T. Marquis, Austin; Jiang-Jen Lin, Round Rock, all of Tex.

[73] Assignee: Texaco Inc., White Plains, N.Y.

[21] Appl. No.: 125,965

[22] Filed: Nov. 27, 1987

[51] Int. Cl.$^4$ .................. C07C 179/025; C07C 31/12

[52] U.S. Cl. ..................................... 568/571; 568/910; 568/910.5

[58] Field of Search ............. 568/571, 575, 910, 910.5

[56] References Cited

U.S. PATENT DOCUMENTS

| | | | |
|---|---|---|---|
| 2,265,948 | 12/1941 | Loder | 560/241 |
| 2,780,654 | 2/1957 | Robertson et al. | 568/860 |
| 2,845,461 | 7/1958 | Winkler et al. | 568/571 |
| 3,474,151 | 10/1969 | Grane | 568/913 |
| 3,825,605 | 7/1974 | Johnston | 568/910 |
| 3,832,149 | 8/1974 | Kozlowski et al. | 568/910 |
| 3,974,228 | 8/1976 | Barone | 568/571 |
| 4,078,423 | 6/1977 | Brownstein et al. | 568/570 |
| 4,296,262 | 10/1981 | Grane et al. | 568/910 |
| 4,296,263 | 10/1981 | Worrell | 568/910 |
| 4,328,365 | 5/1982 | Slinkard et al. | 562/512.2 |
| 4,569,925 | 2/1986 | Yang et al. | 502/209 |

OTHER PUBLICATIONS

Satoru Ito et al, "[Fe$_3$O(OCOR)$_6$L$_3$]$^+$-Catalyzed Epoxidation of Olefinic Alcohol Acetates by Molecular Oxygen," *JACS*, 104, 6450–6452 (1982).

Antony B. Blake and Louis R. Fraser, "Crystal Structure and Mass Spectrum of $\mu_3$-Oxo-Hexakis($\mu$-Trimethylacetato)-Trismethanoltri-Iron(III) Chloride, a Trinuclear Basic Iron(III) Carboxylate," *J.C.S. Dalton*, 193 (1975).

*Primary Examiner*—Donald B. Moyer
*Assistant Examiner*—Bruce D. Gray
*Attorney, Agent, or Firm*—Jack H. Park; Kenneth R. Priem

[57] ABSTRACT

The oxidation of isobutane in the presence of a novel, soluble catalyst of the formula Fe$_3$O(Pivalate)$_6$(MeOH)$_3$Cl is disclosed. Tertiary-Butyl alcohol, tertiary-butyl hydroperoxide, and acetone are produced. A significant increase in isobutane conversion is obtained without a large decrease in selectivity to tertiary-butyl alcohol and tertiary-butyl hydroperoxide using a small amount of catalyst. Tertiary-butyl alcohol is useful as a gasoline additive and tertiary-butyl hydroperoxide is used for the production of propylene oxide. Acetone has a variety of uses as well.

4 Claims, No Drawings

ISOBUTANE OXIDATION IN THE PRESENCE OF A SOLUBLE IRON COMPLEX AS CATALYST

BACKGROUND OF THE INVENTION

Field of the Invention

This invention relates to the oxidation of isobutane to tertiary-butyl alcohol and tertiary-butyl hydroperoxide by catalytic means.

Related Application

This application is related to application Ser. No. 07/125,964. That application concerns the oxidation of isobutane using a vanadium/propylene glycol catalyst.

Description of Related Publications

The catalyst used herein is disclosed for oxidizing certain olefin containing compounds in JACS, 104 6450-6452 (1982).

U.S. Pat. No. 4,328,365 discloses a process for oxidizing lower aliphatic hydrocarbons using a vanadium catalyst.

U.S. Pat. No. 4,569,925 discloses a process for oxidizing aliphatic hydrocarbons using a vanadium catalyst.

Loder, U.S. Pat. No. 2,265,948 employs acetic acid as the solvent for oxidizing isobutane to TBA.

Robertson et al, U.S. Pat. No. 2,780,654 employs benzene as a solvent in oxidizing a mixture of isobutane and isobutene to a mixture of TBA and isobutylene glycol.

Winkler et al, U.S. Pat. No. 2,845,461 oxidizes liquid isobutane in the absence of catalyst to prepare a mixture of TBA and tertiary butyl hydroperoxide (TBHP).

Grane, U.S. Pat. No. 3,474,151 heats TBA at 375°–475° F. for a few minutes, whereby traces of TBHP are thermally decomposed to provide a TBA suitable for blending into gasoline.

Johnston, U.S. Pat. No. 3,825,605 oxidizes isobutane to TBA using a solid catalyst comprising molybdenum oxide, and minor amounts of two other metals (from a group comprising cobalt, iron, or chromium).

Kozlowski et al, U.S. Pat. No. 3,832,149 prepares a motor fuel consisting of a mixture of alkylate and an oxylate prepared by hydrogenating the oxidate derived from oxidizing isobutane.

Barone, U.S. Pat. No. 3,974,228, employs a buffer such as lanthanum carbonate in oxidizing isobutane to TBHP.

Browntein et al, U.S. Pat. No. 4,028,423 oxidizes isobutane to TBA and TBHP using a copper polyphthalocyanine catalyst activated with an aromatic amine.

U.S. Pat. No. 4,296,263 describes the oxidation of isobutane/n-butane mixtures in the presence of chromium, copper, nickel, manganese, molbydenum, etc.

U.S. Pat. No. 4,296,262 describes the oxidation of isobutane in the presence of molybdenum.

The present invention to be described below is a method of preparing tertiary-butyl alcohol, as well as tertiary-butyl hydroperoxide, by the oxidation of isobutane in the presence of an iron complex.

SUMMARY OF THE INVENTION

In accordance with the present invention, isobutane is oxidized with an oxygen-containing material to produce a liquid effluent comprising both tertiary butyl alcohol (TBA) and tertiary butyl hydroperoxide (TBHP) in the presence of an effective amount of a soluble complex which may be represented by the formula $Fe_3O(pivalate)_6(MeOH)_3Cl$.

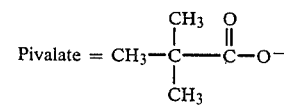

DESCRIPTION OF THE PREFERRED EMBODIMENTS

The soluble propylene iron complex catalyst is described by Blake and Fracer in J. Chem. Soc., Dalton Trans., 193 (1975). The preparation of the catalyst is described in detail in the examples which follow, but generally, pivalic acid is dissolved in water containing sodium hydroxide. This mixture is then added dropwise to iron chloride dissolved in water. After stirring, the solids are collected with suction, washed with water and recrystallized from methanol/chloroform.

It should be noted that these complexes are surprisingly made very simply at mild temperatures and with short reaction times. The complexes require very little or no filtration and appear to remain stable indefinitely. In addition, the processing costs and reactant costs to make these complexes are minimal.

The complexes and method of this invention are more particularly illustrated by the examples which follow which should not be construed as limiting the invention in any way.

The oxidation of isobutane with the catalyst described above is typically conducted by reacting an isobutane with an oxygen in the presence of the catalyst and a solvent which can be tertiary butyl alcohol (TBA). The products are principally tertiary butyl alcohol (TBA), tertiary butyl hydroperoxide (TBHP) and acetone.

Pure oxygen can be used. Also, air and mixtures of oxygen with inert materials are examples of useful materials to oxidize the isobutane. One skilled in the art would be aware of various useful oxygen-containing materials.

Preferably, the catalyst concentration is from about 5 to 5000 ppm based on the combination of the olefin and the organic hydroperoxide. Further, the reaction should be conducted at a temperature in the range of about 125° C. to 185° C., preferably about 134° C. to 165° C. and especially in the range of about 145° C. to 155° C. The pressure should be maintained within the range from about 300 to 1500 psig, preferably about 400 to 800 at residence time of from about 0.5 to 10.0 hours, preferably from 2 to 6 hours. By method of this invention a significant increase in isobutane conversion is obtained without a large decrease in selectivity to TBA and TBHP using a very small amount of catalyst. Of course, higher conversion of isobutane will yield more TBA and lower conversion will yield more TBHP. The parameters above can be easily controlled by skilled art workers to achieve the results desired.

EXAMPLE 1

Preparation of $Fe_3O(piv)_6(MeOH)_3Cl$

The method below is similar to that described by Blake and Fracer in J. Chem. Soc., Dalton Trans., 193 (1975).

Pivalic acid (25.5 g, 0.25 mol) was dissolved in 50 ml H$_2$O containing NaOH (10.0 g, 0.25 mol). This was added dropwise to FeCl$_3$.6H$_2$O (67.5 g, 0.25 mol) dissolved in 300 ml H$_2$O. After the addition was complete, the mixture was stirred an additional 5 minutes and the solid collected with suction and washed with water. The solid was dried for 20 hours at ambient temperature and recrystallized from CHCl$_3$/MeOH.

excess of oxygen would not be present to create an explosive mixture. The reaction mixture was then cooled as rapidly as possible to ambient temperature and the contents of the autoclave pressured out into a tared stainless steel bomb with 300 psi nitrogen. The products were determined by GC and are shown in the attached table. Small amounts of acids and other products were also formed.

TABLE

Oxidation of Isobutane in the Presence of a Novel Iron Complex Catalyst of Example 1

| N.B. Number | Remarks[a,b] | Time Hr. | Temp °C. | Conv. (%) | Selectivity, % | | |
|---|---|---|---|---|---|---|---|
| | | | | | TBHP | TBA | Acetone |
| 5973-91 | 0.030 g Complex in Dioxolane (0.600 g) | 2.0 | 145 | 21.95 | 22.02 | 75.58 | 5.212 |
| 5979-93 | 0.025 g Complex | 4.0 | 145 | 44.63 | 22.53 | 69.81 | 7.563 |
| 5979-2 | 0.055 g Complex in Dioxolane (0.700 g) | 2.0 | 145 | 27.88 | 8.43 | 70.73 | 20.764 |
| 5987-7 | 0.049 g Complex | 4.0 | 145 | 46.65 | 13.47 | 74.12 | 12.31 |
| 5987-16 | 0.110 g Complex | 4.0 | 145 | 51.76 | 7.31 | 75.31 | 17.29 |
| 5987-59 | Control | 4.0 | 145 | 30.08 | 52.80 | 44.41 | 2.467 |
| 5987-79 | Control | 4.0 | 145 | 29.88 | 53.03 | 44.16 | 2.561 |

[a]Complex = Fe$_3$O(Pivalate)$_6$(MeOH)$_3$Cl
[b]About 100 g TBHP + TBA + IB charged IR analysis indicated the presence of a strong bond at 1580 cm$^{-1}$ and also at 1430 cm$^{-1}$ typical of carboxylate salts.

Analysis by atomic adsorption indicated the presence of 19.3 wt % Fe (theory 18.5 wt %).

EXAMPLE 2

Procedure

A mixture of TBHP and TBA equivalent to 5-6% conversion (and catalyst, if any) was charged through a small vent hole near the top of the reactor. The autoclave was sealed and 95 g isobutane pressured in. The mixture was then heated to the desired temperature. Oxygen was added in approximately 1 gram increments until a pressure of 150-200 psi over autogeneous was reached. Oxygen was then added only after the pressure had dropped approximately 50 psi. The reaction was continued for the desired time, and near the end of the reaction, no more oxygen was added so that a large

We claim:

1. The method for oxidizing isobutane with an oxygen-containing material in the presence of an effective amount of a soluble catalyst of the formula Fe$_3$O(Pivalate)$_6$(MeOH)$_3$Cl.

2. The method of claim 1 wherein the catalyst concentration is about 5 to 5000 ppm.

3. The method as in claim 1 wherein the reaction is conducted at a temperature in the range of about 125° C. to 185° C. and at a pressure in the range from about 300 to 1500-psig.

4. The method for oxidizing isobutane comprising reacting isobutane with an oxygen-containing material in the presence of a soluble catalyst of the formula Fe$_3$O(Pivalate)(MeOH)$_3$Cl wherein the catalyst concentration is about 5 to 5000 ppm, the temperature is in the range from about 125° C. to 185° C. and the pressure is in the range from about 300 to 1500 psig.

* * * * *